(12) United States Patent
Elsheikh et al.

(10) Patent No.: US 6,479,718 B1
(45) Date of Patent: Nov. 12, 2002

(54) LIQUID PHASE PROCESS FOR HCFC-123

(75) Inventors: Maher Y. Elsheikh, Tredyffrin, PA (US); Jonathan M. Tracy, Pottstown, PA (US); John A. Wismer, Lower Makefield, PA (US)

(73) Assignee: Atofina Chemicals, Inc., Philadelphia, PA (US)

( * ) Notice: Subject to any disclaimer, the term of this patent is extended or adjusted under 35 U.S.C. 154(b) by 0 days.

(21) Appl. No.: 10/108,607

(22) Filed: Mar. 28, 2002

(51) Int. Cl.$^7$ ................................................ C07C 17/08

(52) U.S. Cl. ........................ 570/167; 570/165; 570/166; 570/168; 570/169

(58) Field of Search ................................. 570/167, 165, 570/166, 168, 169

(56) References Cited

U.S. PATENT DOCUMENTS 6,049,016 A    4/2000   Yoshimura et al. ......... 570/169

*Primary Examiner*—Alan Siegel
(74) *Attorney, Agent, or Firm*—William D. Mitchell

(57) ABSTRACT

An improved liquid phase process is provided for the fluorination of perchloroethylene to 1,1-dichloro-2,2,2-trifluoroethane in the presence of an antimony catalyst.

7 Claims, No Drawings

LIQUID PHASE PROCESS FOR HCFC-123

BACKGROUND OF THE INVENTION

This invention relates to an improved liquid phase process for preparing 1,1-dichloro-2,2,2-trifluoroethane ("HCFC-123" or "123") by the catalyzed fluorination of perchloroethylene ("PERC") in the presence of hydrogen fluoride ("HF"), particularly to a process which involves the use of a catalyst consisting essentially of an antimony (V) catalyst. HCFC-123 is particularly useful as an intermediate for making pentafluoroethane ("HFC-125" or "125"), a known refrigerant.

U.S. Pat. No. 6,049,016 also discloses a liquid phase process for preparing 123 by the catalyzed fluorination of PERC in the presence of HF, but in its example using an antimony catalyst, a mixture of SbF3 and SbF5, a substantial amount of the olefin 1112a (CCl2=CF2) was produced. Since the boiling point of this olefin (19° C.) and 123 (27° C.) are close, separation by distillation can be expected to be difficult and require an expensive chemical treatment such as adsorption or conversion of the 1112a to a higher boiling compound. If the olefin is not separated, presence of the olefin can be expected to result in faster deactivation of catalyst used when the 123 is converted to 125. Thus, it would be useful to have a process which avoids the formation of olefin impurities.

BRIEF SUMMARY OF THE INVENTION

An improved liquid phase process for preparing 123 by the catalyzed fluorination of PERC in the presence of HF is provided, which improvement comprises using a catalyst consisting essentially of an antimony (V) catalyst such as SbF5. An unsupported or supported catalyst may be used, the support typically being carbon. Because the catalyst is corrosive in the presence of HF, a preferred embodiment involves the use of a reactor made out of or lined with a fluororesin such as polytetrafluoroethylene ("PTFE"). Particularly preferred is the use of an adiabatic fluororesin reactor since the heat liberated by the exothermic PERC to 123 reaction will supply most of the heat of rectification to remove the 123 and by-product HCl as a vapor from the system. The 123 can then be readily converted to 125 by known processes, such as by fluorinating the 123 with HF in a gas phase process in the presence of a fluorination catalyst such as a supported or unsupported Cr(III)-based catalyst.

DETAILED DESCRIPTION

It has now been found that use of an antimony (V) catalyst in the liquid phase fluorination of PERC to 123 avoids formation of olefin impurities such as 1112a. The higher the fluorine content of the Sb (V) catalyst the better, SbF4Cl or, preferably, SbF5 thus being the most active species. The catalyst may be unsupported or it may be used on a support such as carbon, graphite, alumina, or fluorided alumina.

The process of this invention can be conducted as a batch or continuous process. Inorganic solvent, such as excess HF, or organic solvent, such as excess PERC or a hydrochlorofluorocarbon ("HCFC") such as 123, 1,1,2-trichloro-2,2-difluoroethane ("122") or 1,1,2,2-tetrachloro-2-fluoroethane ("121"), or mixtures of such solvents may also be present. Thus, in a continuous reaction, 122 and 121 by-products can be fed back to the reactor. The HF:PERC molar ratio is typically from 1 to 50, preferably from 2 to 10. The temperature is typically from 20 to 300° C., preferably from 50 to 200° C. The pressure is typically from about 50 to 600 psig, preferably from 100 to 300 psig. The by-product HCl can be removed from the resultant reaction mixture by methods known in the art such as by absorption (in water or caustic) or by distillation. The HCl can also be continuously removed from the reactor during the reaction by distillation.

To convert 123 to 125 in a gas phase fluorination reaction, 123 and excess HF are typically reacted in the presence of an oxygen-containing gas such as air, to maintain catalyst activity, and a Cr (III)-based catalyst such as chromium oxide. A cocatalyst such as Ni (II), Co (II), Zn (II) or the like may also be used. Typical operating temperatures and pressures are 200–400° C. and 1–10 atmospheres (preferably 1–6 atmospheres). The molar ratio of HF to 123 is typically 2–10.

The practice of the invention is illustrated in more detail in the following non-limiting examples.

EXAMPLE 1

A liquid phase mixture of HF and PERC, at a 26 to 1 molar ratio was reacted in an autoclave in the presence of SbF5 catalyst at a pressure of 185 psig and a temperature of 130° C. for about 2.8 hours. Conversion of PERC was over 98% and selectivity for 123 was over 91%. The major coproduct was 122.

EXAMPLE 2

Example 1 was repeated except that the reaction was carried out in the presence of 123 as a solvent, the temperature was 90° C., the pressure was 180 psig, and the HF/PERC ratio was 6.7. GC (gas chromatography) analysis showed conversion of about 90% and selectivity for 123 of about 77%. Major coproducts were 124 and 122.

We claim:

1. In a liquid phase process for preparing 1,1-dichloro-2,2,2-trifluoroethane by the catalyzed fluorination of perchloroethylene in the presence of hydrogen fluoride, the improvement which comprises using a catalyst consisting essentially of antimony pentafluoride.

2. The process of claim 1 wherein the process is performed in the presence of one or more solvents selected from the group consisting of a hydrochlorofluorocarbon, excess HF or excess perchloroethylene.

3. The process of claim 1 wherein the catalyst is supported on carbon.

4. The process of claim 1 wherein the process is carried out using a reactor made of or lined with a fluororesin.

5. The process of claim 1 wherein the process is carried out in the presence of an adiabatic fluororesin reactor.

6. The process of claim 5 wherein the fluororesin is polytetrafluoroethylene.

7. A process for preparing pentafluoroethane which comprises (a) preparing 1,1-dichloro-2,2,2-trifluoroethane by the process of claim 1 and (b) fluorinating said 1,1-dichloro-2,2,2-trifluoroethane with hydrogen fluoride in a gas phase process in the presence of a fluorination catalyst.

* * * * *